United States Patent [19]

Yonek et al.

[11] Patent Number: 5,561,200

[45] Date of Patent: Oct. 1, 1996

[54] BLOCKED POLYISOCYANATES WITH IMPROVED THERMAL STABILITY

[75] Inventors: Kenneth P. Yonek, McMurray; Lyuba K. Gindin, Pittsburgh; Douglas A. Wicks, Mt. Lebanon, all of Pa.

[73] Assignee: Bayer Corporation, Pittsburgh, Pa.

[21] Appl. No.: 449,405

[22] Filed: May 23, 1995

[51] Int. Cl.⁶ .............. C08G 18/80; C07D 233/78; C07D 403/02; C07D 403/14

[52] U.S. Cl. ............... 528/45; 528/49; 528/68; 528/73; 528/75; 528/84; 548/300.1; 548/312.3; 548/313.7; 548/314.1; 548/314.4

[58] Field of Search ............. 528/45, 49, 68, 528/73, 75, 84; 548/300.1, 312.1, 313.7, 314.1, 314.4

[56] References Cited

U.S. PATENT DOCUMENTS

| | | | |
|---|---|---|---|
| 3,549,599 | 12/1970 | Merten | 528/73 |
| 3,639,418 | 2/1972 | Merten | 548/314.1 |
| 4,702,953 | 10/1987 | Jonas et al. | 428/209 |
| 5,126,170 | 6/1992 | Zwiener et al. | 427/385.5 |
| 5,236,741 | 8/1993 | Zwiener et al. | 427/385.5 |
| 5,243,012 | 9/1993 | Wicks et al. | 528/58 |
| 5,412,056 | 5/1995 | Zwiener et al. | 528/73 |
| 5,461,135 | 10/1995 | Malofsky et al. | 528/60 |
| 5,506,327 | 4/1996 | Yonek et al. | 528/45 |

FOREIGN PATENT DOCUMENTS 0133519  2/1985  European Pat. Off. .

*Primary Examiner*—James J. Seidleck
*Assistant Examiner*—Rabon Sergent
*Attorney, Agent, or Firm*—Joseph C. Gil; Thomas W. Roy

[57] ABSTRACT

The present invention relates to blocked polyisocyanates containing at least one isocyanate group which is reversibly blocked with a monofunctional blocking agent for isocyanate groups and at least one isocyanate group in the form of a thermally stable hydantoin group. The present invention also relates to one-component coating compositions containing these blocked polyisocyanates and compounds containing isocyanate-reactive groups.

9 Claims, No Drawings

BLOCKED POLYISOCYANATES WITH IMPROVED THERMAL STABILITY

BACKGROUND OF THE INVENTION

1. Field of the Invention

The present invention relates to blocked polyisocyanates containing at least one reversibly blocked isocyanate group and at least one isocyanate group in the form of a thermally stable hydantoin group and to their use, optionally in combination with compounds containing isocyanate-reactive groups, especially in electrodeposition coating applications.

2. Description of the Prior Art

Coating compositions containing blocked polyisocyanates are commonly used in the coating industry for the production of one-component coating compositions. Because the isocyanate groups are blocked, they are not reactive under ambient conditions with the isocyanate-reactive component present in the coating composition. However, when the composition is heated to elevated temperatures the blocking agent is released to reform isocyanate groups, which then react with the isocyanate-reactive component to form a coating.

In certain blocked polyisocyanates used in the coatings industry both of the isocyanate groups of the starting polyisocyanate are not reacted with blocking agents. For example, in blocked NCO prepolymers the diisocyanate in the terminal position has one blocked isocyanate group and one isocyanate group which is reacted with, e.g., a polyol. Alternatively, in the production of electrodeposition coatings one of the isocyanate groups of 2,4-diisocyanatotoluene is blocked with a blocking agent, such as a primary alcohol, while the remaining isocyanate group is either reacted with a high molecular weight polymer having pendant amino and/or hydroxyl groups or it is reacted with a low molecular weight compounds having such groups and blended with the high molecular weight polymer.

One of the disadvantages of these compositions is that during the final cure at elevated temperatures the isocyanate group attached to the polymer unblocks (i.e., converts to an isocyanate group and a hydroxyl or amino group) at approximately the same temperature as the blocked isocyanate group becomes unblocked. When both sides become detached (unblocked), the diisocyanate monomer, e.g., TDI, tends to migrate to the surface, where it can cause discoloration, e.g., of subsequently applied coating layers.

It is object of the present invention to overcome this problem by providing blocked polyisocyanates in which it is possible to unblock the blocked isocyanate group without unblocking any isocyanate groups which are not intended to be unblocked.

This object may be achieved with the blocked polyisocyanates according to the present invention described hereinafter.

SUMMARY OF THE INVENTION

The present invention relates to blocked polyisocyanates containing at least one isocyanate group which is reversibly blocked with a monofunctional blocking agent for isocyanate groups and at least one isocyanate group in the form of a thermally stable hydantoin group, wherein the blocked polyisocyanates correspond to the formula

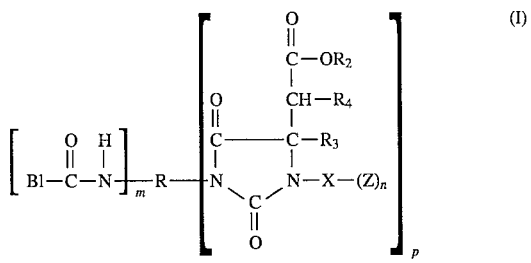

wherein

X represents an organic group which has a valency of n+1 and is inert towards isocyanate groups at a temperature of 100° C. or less, R represents the residue obtained by removing the isocyanate groups from a polyisocyanate having a functionality of m+p, $R_2$ represents an optionally substituted hydrocarbon radical, $R_3$ and $R_4$ may be identical or different and represent hydrogen or organic groups which are inert towards isocyanate groups at a temperature of 100° C. or less, BI represents the residue of a reversible, monofunctional blocking agent for isocyanate groups, m has a value of 1 to 5, n has a value of 1 to 3, p has a value of 1 to 5, m+p is 2 to 6 and Z represents —OH, —COOH, a polymer backbone or a group corresponding to the formula

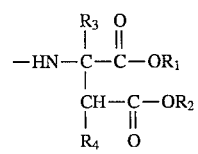

wherein $R_1$ represents an optionally substituted hydrocarbon radical.

The present invention also relates to a one-component coating composition containing this blocked polyisocyanate and a compound containing isocyanate-reactive groups.

DETAILED DESCRIPTION OF THE INVENTION

Examples of suitable polyisocyanate starting materials which may be used to prepare the blocked polyisocyanates according to the present invention include monomeric diisocyanates and polyisocyanate adducts, preferably monomeric diisocyanates and more preferably monomeric diisocyanates in which the isocyanate groups do not have the same reactivity with isocyanate-reactive groups.

Suitable monomeric diisocyanates may be represented by the formula $$R(NCO)_2$$

in which R represents an organic group obtained by removing the isocyanate groups from an organic diisocyanate having a molecular weight of about 112 to 1,000, preferably about 140 to 400. Diisocyanates preferred for the process according to the invention are those represented by the above formula in which R represents a divalent aliphatic hydrocarbon group having 4 to 18 carbon atoms, a divalent cycloaliphatic hydrocarbon group having 5 to 15 carbon atoms, a divalent araliphatic hydrocarbon group having 7 to 15 carbon atoms or a divalent aromatic hydrocarbon group having 6 to 15 carbon atoms.

Examples of the suitable organic diisocyanates include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis-(4-isocyanatocyclohexyl)-methane, 2,4'-dicyclohexyl-methane diisocyanate, 1,3- and 1,4-bis-(isocyanatomethyl)-cyclohexane, bis-(4-isocyanato-3-methyl-cyclohexyl)-methane, α,α, α',α'-tetramethyl-1,3- and/or -1,4-xylylene diisocyanate, 1-isocyanato-1-methyl-4(3)-isocyanatomethyl cyclohexane, 2,4- and/or 2,6-hexahydrotoluylene diisocyanate, 1,3- and/or 1,4-phenylene diisocyanate, 2,4- and/or 2,6-toluylene diisocyanate, 2,4- and/or 4,4'-diphenyl-methane diisocyanate, 1,5-diisocyanato naphthalene and mixtures thereof. Polyisocyanates containing 3 or more isocyanate groups such as 4-isocyanantomethyl-1,8-octamethylene diisocyanate and aromatic polyisocyanates such as 4,4',4"-triphenyl-methane triisocyanate and polyphenyl polymethylene polyisocyanates obtained by phosgenating aniline/formaldehyde condensates may also be used.

Preferred organic diisocyanates are those from the preceding list in which the isocyanate groups do not have the same reactivity with isocyanate-reactive groups, especially 1-isocyanato-3-isocyanatomethyl-3,5,5-trimethyl-cyclohexane (isophorone diisocyanate or IPDI), 1,3-bis-(isocyanatomethyl)-cyclohexane, 1-isocyanato-1-methyl-4(3)-isocyanatomethyl cyclohexane, 2,4-hexahydrotoluylene diisocyanate, 2,4-toluylene diisocyanate and 2,4-diphenyl-methane diisocyanate. Most preferred is 2,4-toluylene diisocyanate.

In accordance with the present invention the polyisocyanate component may also be in the form of a polyisocyanate adduct. Suitable polyisocyanate adducts are those containing isocyanurate, uretdione, biuret, urethane, allophanate, carbodiimide and/or oxadiazinetrione groups. The polyisocyanates adducts have an average functionality of 2 to 6 and an NCO content of 5 to 30% by weight.

1) Isocyanurate group-containing polyisocyanates which may be prepared as set forth in DE-PS 2,616,416, EP-OS 3,765, EP-OS 10,589, EP-OS 47,452, U.S. Pat. No. 4,288, 586 and U.S. Pat. No. 4,324,879. The isocyanato-isocyanurates generally have an average NCO functionality of 3 to 3.5 and an NCO content of 5 to 30%, preferably 10 to 25% and most preferably 15 to 25% by weight.

2) Uretdione diisocyanates which may be prepared by oligomerizing a portion of the isocyanate groups of a diisocyanate in the presence of a suitable catalyst, e.g., a trialkyl phosphine catalyst, and which may be used in admixture with other aliphatic and/or cycloaliphatic polyisocyanates, particularly the isocyanurate group-containing polyisocyanates set forth under (1) above.

3) Biuret group-containing polyisocyanates which may be prepared according to the processes disclosed in U.S. Pat. Nos. 3,124,605; 3,358,010; 3,644,490; 3,862,973; 3,906, 126; 3,903,127; 4,051,165; 4,147,714; or 4,220,749 by using co-reactants such as water, tertiary alcohols, primary and secondary monoamines, and primary and/or secondary diamines. These polyisocyanates preferably have an NCO content of 18 to 22% by weight and an average NCO functionality of 3to3.5.

4) Urethane group-containing polyisocyanates which may be prepared in accordance with the process disclosed in U.S. Pat. No. 3,183,112 by reacting excess quantities of polyisocyanates, preferably diisocyanates, with low molecular weight glycols and polyols having molecular weights of less than 400, such as trimethylol propane, glycerine, 1,2-dihydroxy propane and mixtures thereof. The urethane group-containing polyisocyanates have a most preferred NCO content of 12 to 20% by weight and an (average) NCO functionality of 2.5 to 3.

5) Allophanate group-containing polyisocyanates which may be prepared according to the processes disclosed in U.S. Pat. Nos. 3,769,318, 4,160,080 and 4,177,342. The allophanate group-containing polyisocyanates have a most preferred NCO content of 12 to 21% by weight and an (average) NCO functionality of 2 to 4.5.

6) Isocyanurate and allophanate group-containing polyisocyanates which may be prepared in accordance with the processes set forth in U.S. Pat. Nos. 5,124,427, 5,208,334 and 5,235,018, the disclosures of which are herein incorporated by reference, preferably polyisocyanates containing these groups in a ratio of monoisocyanurate groups to mono-allophanate groups of about 10:1 to 1:10, preferably about 5:1 to 1:7.

7) Carbodiimide group-containing polyisocyanates which may be prepared by oligomerizing di- or polyisocyanates in the presence of known carbodiimidization catalysts as described in DE-PS 1,092,007, U.S. Pat. No. 3,152,162 and DE-OS 2,504,400, 2,537,685 and 2,552,350.

8) Polyisocyanates containing oxadiazinetrione groups and containing the reaction product of two moles of a diisocyanate and one mole of carbon dioxide.

Preferred polyisocyanate adducts are the polyisocyanates containing isocyanurate groups, biuret groups and mixtures of isocyanurate groups with either allophanate or uretdione groups. However, the use of polyisocyanate adducts are less preferred according to the invention since the isocyanate groups of these adducts generally have the same reactivity.

The functionality of the polyisocyanates, which corresponds to "m+p" in formula I, is 2 to 6, preferably 2 to 4 and more preferably 2.

To prepare the blocked polyisocyanates according to the invention the isocyanate groups of the starting polyisocyanate are reacted with a reversible, monofunctional blocking agent for isocyanate groups and an aspartic acid ester. The blocking reaction is carried out in known manner by reacting the isocyanate groups with suitable blocking agents, preferably at an elevated temperature (e.g., about 40° to 160° C.), and optionally in the presence of a suitable catalyst, such as a tertiary amine or metal salt.

Suitable blocking agents include monophenols such as phenol, the cresols, the trimethylphenols and the tert. butyl phenols; primary, secondary or tertiary alcohols such as methanol, ethanol, n-propanol, isopropanol, n-butanol, isobutanol, the isomeric pentanols, hexanols and octanols (including branched alcohols such as 2-ethyl hexanol), tert. butanol, tert. amyl alcohol, butyl carbitol, dimethylphenyl carbinol and glycol ethers such as propylene glycol monomethyl ether; compounds which easily form enols such as acetoacetic ester, acetyl acetone and malonic acid derivatives, e.g. malonic acid diethylester; secondary aromatic amines such as N-methyl aniline, the N-methyl toluidine, N-phenyl toluidine and N-phenyl xylidine; imides such as succinimide; lactams such as ε-caprolactam and δ-valerolactam; oximes such as methyl ethyl ketoxime (butanone oxime), methyl amyl ketoxime and cyclohexanone oxime; mercaptans such as methyl mercaptan, ethyl mercaptan, butyl mercaptan, 2-mercapto-benzthiazole, α-naphthyl mercaptan and dodecyl mercaptan; and triazoles such as 1H-1, 2,4-triazole. Preferred blocking agents are the primary monoalcohols such as 2-ethylhexanol.

The isocyanate groups that are not blocked are reacted with an aspartic acid ester which contains at least two isocyanate-reactive groups. The aspattic acid ester corresponds to the formula:

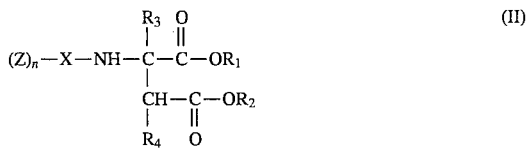

wherein

X represents an organic group which has a valency of n+1 and is inert towards isocyanate groups at a temperature of 100° C. or less, preferably having a molecular weight of less than 600 and more preferably an aliphatic, cycloaliphatic, araliphatic or aromatic radical having 2 to 15 carbon atoms, $R_1$ and $R_2$ may be the same or different and represent optionally substituted hydrocarbon radicals, preferably an alkyl radical containing 1 to 9 carbon atoms, more preferably methyl, ethyl or butyl, or $R_1$ and $R_2$ together with the p-carbon atom form a cycloaliphatic or heterocyclic ring, $R_3$ and $R_4$ may be identical or different and represent hydrogen or organic groups which are inert towards isocyanate groups at a temperature of 100° C. or less, preferably hydrogen, and Z represents —OH, —COOH, a polymer backbone or a group corresponding to the formula

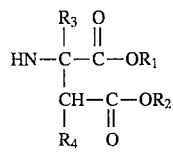

n has a value of 1 to 3, preferably 1 or 2 and more preferably 1.

The aspartic acid ester may be prepared in known manner by reacting primary amine-containing compounds corresponding to the formula $$(Y)_s—X—(NH_2)_t \qquad (III)$$

wherein

Y represents —OH or —COOH, s has a value of 0 to 3, preferably 0 to 1 and more preferably 0 when "t" is 2 and 1 when "t" is 1, and t has a value of 1 to 4, preferably 1 or 2 and s+t is 2 to 4, preferably 2.

with optionally substituted maleic or fumaric acid esters corresponding to the formula

The polyamines include high molecular weight amines having molecular weights of 800 to about 10,000, preferably 800 to about 6,000, and low molecular weight amines having molecular weights below 800, preferably below 600. The molecular weights are number average molecular weights ($M_n$) and are determined by end group analysis (NH number). Examples of these polyamines are those wherein the amino groups are attached to aliphatic, cycloaliphatic, araliphatic and/or aromatic carbon atoms.

Suitable low molecular polyamines include ethylene diamine, 1,2- and 1,3-propane diamine, 2-methyl-1,2-propane diamine, 2,2-dimethyl-1,3-propane diamine, 1,3- and 1,4-butane diamine, 1,3- and 1,5-pentane diamine, 2-methyl-1,5-pentane diamine, 1,6-hexane diamine, 2,5-dimethyl-2,5-hexane diamine, 2,2,4- and/or 2,4,4-trimethyl-1,6-hexane diamine, 1,7-heptane diamine, 1,8-octane diamine, 1,9-nonane diamine, triaminononane, 1,10-decane diamine, 1,11 -undecane diamine, 1,12-dodecane diamine, 1-amino-3-aminomethyl-3,5,5-trimethyl cyclohexane, 2,4- and/or 2,6-hexahydrotoluylene diamine, 2,4'- and/or 4,4'-diamino-dicyclohexyl-methane, 3,3'-dialkyl-4,4'-diamino-dicyclohexyl methanes (such as 3,3'-dimethyl-4,4'-diamino-dicyclohexyl methane and 3,3'-diethyl-4,4'-diamino-dicyclohexyl methane), 1,3- and/or 1,4-cyclohexane diamine, 1,3-bis(methylamino)-cyclohexane, 1,8-p-menthane diamine, hydrazine, hydrazides of semicarbazido carboxylic acids, bis-hydrazides, bis-semicarbazides, phenylene diamine, 2,4- and 2,6-toluylene diamine, 2,3- and 3,4-toluylene diamine, 2,4'- and/or 4,4'-diaminodiphenyl methane, higher functional polyphenylene polymethylene polyamines obtained by the aniline/formaldehyde condensation reaction, N,N,N-tris-(2-amino-ethyl)-amine, guanidine, melamine, N-(2-aminoethyl)-1,3-propane diamine, 3,3'-diamino-benzidine, polyoxypropylene amines, polyoxyethylene amines, 2,4-bis-(4'-aminobenzyl)-aniline and mixtures thereof. Also suitable are amine-terminated polyethers having the required molecular weight such as the Jeffamine resins, e.g., Jeffamine D-230 and T-403, available from Huntsman.

Suitable high molecular weight polyamines include those prepared from the known polyhydroxyl compounds of polyurethane, especially the polyethers. The polyamines may be prepared by reacting the polyhydroxyl compounds with an excess of the previously described polyisocyanates to form NCO prepolymers and subsequently hydrolyzing the terminal isocyanate group to an amino group. Preferably, the polyamines are prepared by convening the terminal hydroxy groups of the polyhydroxyl compounds to amino groups, e.g., by amination. Preferred high molecular weight polyamines are amine-terminated polyethers such as the Jeffamine resins available from Huntsman.

Preferred polyamines are 1-amino-3-aminomethyl-3,5,5-trimethylo-cyclohexane (isophorone diamine or IPDA), bis-(4-aminocyclohexyl)methane, bis-(4-amino-3-methylcyclohexyl)-methane, 1,6-diamino-hexane, 2-methyl pentamethylene diamine, ethylene diamine, triaminononane, 2,4- and/or 2,6-toluylene diamine, 4,4'- and/or 2,4'-diaminodiphenyl methane and the Jeffamine D-230 and T-403 resins.

Also suitable are aminoalcohols and aminoacids such as ethanolamine, 1-amino-2-hydroxypropane, 1-amino-3-hydroxypropane, 1-hydroxy-2-aminopropane and 1,3-propanolamine, the isomeric butanol amines, 2-amino-1,3-propane diol and 2-amino-2-hydroxymethyl-propane diol and the corresponding aminoacids. Especially preferred are ethanolamine, the isomeric propanolamines and the corresponding aminoacids.

Preferred examples of optionally substituted maleic or fumaric acid esters suitable for use in the preparation of the compounds corresponding to formula II include dimethyl, diethyl and di-n-butyl esters of maleic acid and fumaric acid and the corresponding maleic or fumaric acid esters substituted by methyl in the 2- and/or 3-position.

The preparation of the aspartic acid esters corresponding to formula II from the above mentioned starting materials may be carried out, for example, at a temperature of 0° to 100° C. using the starting materials in such proportions that at least 1, preferably 1, olefinic double bond is present for each primary amino group. Excess starting materials may be removed by distillation after the reaction. The reaction may be carried out solvent-free or in the presence of suitable solvents such as methanol, ethanol, propanol, tetrahydrofuran, dioxane and mixtures of such solvents.

The blocked polyisocyanates according to the invention are generally prepared by reacting the polyisocyanate starting material with the monofunctional blocking agent under the conditions previously set forth before reacting the starting material with the aspartic acid ester. The blocking agent is used in an amount which is sufficient to block one of the isocyanate groups of a diisocyanate and at least one, but not all of the isocyanate groups of a polyisocyanate. When a diisocyanate having isocyanate groups with different reactivity is used as the starting material, the blocking agent should most preferably be used in an amount that is sufficient to react with the more reactive isocyanate group.

The isocyanate groups that are not blocked are subsequently reacted with the aspartic acid ester containing secondary amino groups to initially form urea groups. The amount of these secondary amino groups is selected such that one mole of the aspartic acid ester is present for each equivalent of isocyanate groups. For example, one mole of a bis-aspartate or a hydroxy group-containing aspartate is reacted with each equivalent of isocyanate groups. The urea group-forming reaction is carried out at a temperature of 10° to 100° C., preferably 20° to 80° C. and more preferably 20° to 50° C.

After the reaction with the blocking agent and the aspartic acid ester, the blocked polyisocyanates according to the invention are heated to a temperature of 60° to 240° C., preferably 80° to 160° C. and more preferably 100° to 140° C., to convert the aspartate esters to the corresponding hydantoin with elimination of a monoalcohol corresponding to the formula $R_1OH$ and/or $R_2OH$. Instead of forming the urea groups and hydantoin groups in two steps, the reaction may be carried out entirely at elevated temperatures in order to form the urea groups and hydantoin groups in one step.

The invention may be represented by the following reaction scheme using a diisocyanate starting material (in which one of the isocyanate groups is blocked with a blocking agent) and an aspartic acid ester prepared from a dialkyl maleate and an amino alkyl alcohol:

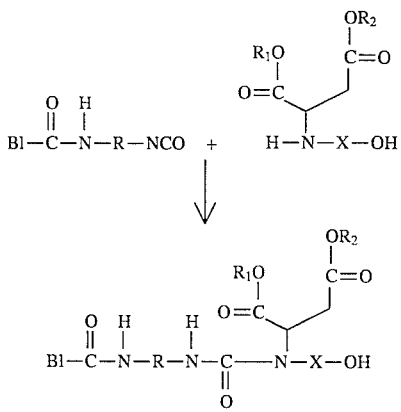

Once formed, the hydantoin groups are thermally stable and do not undergo any chemical change at the temperatures necessary to release the blocking agent.

The blocked polyisocyanates according to the invention may be self polymerized in the absence of an additional reaction component by heating to an elevated temperature of 100° to 250° C., preferably 120° to 200° C., which is sufficient to release the blocking agent and reform the isocyanate group. Any urea groups formed by reacting the unblocked isocyanate groups with the aspartic acid esters, which may be present as "Z" groups, are converted to hydantoin groups at the temperatures necessary to release the blocking agents.

In addition to curing by self polymerization, the blocked polyisocyanates may be blended with or incorporated into other high molecular weight polymers containing isocyanate-reactive groups. The secondary amino groups, hydroxyl groups or carboxylic acid groups, can be used to chemically bind the polyisocyanates to these polymers via the formation of ether, ester or amide groups or by the addition of secondary amino groups to ethylenically unsaturated groups by the Michel addition. The resulting product is a high molecular polymer which contains pendant blocked isocyanate groups and also pendant isocyanate-reactive groups such as amino groups, hydroxyl groups or carboxylic acid groups. These products can be cross-linked by heating to elevated temperatures which are sufficient to release the blocking agent.

Alternatively, the blocked polyisocyanates according to the invention may be prepared by first preparing a polymer having a pendant aspartate group, e.g., by the preceding reaction mechanisms, and then reacting the pendant aspartate group with the partially blocked polyisocyanate. It is also possible to conduct the blocking reaction after reacting an unblocked polyisocyanate with the pendant aspartate group. The blocked polyisocyanates according to the invention are especially suited for use in combination with electrodeposition resins.

To accelerate hardening, the coating compositions may contain known polyurethane catalysts, e.g., tertiary amines such as triethylamine, pyridine, methyl pyridine, benzyl dimethylamine, N,N-dimethylamino cyclohexane, N-methyl-piperidine, pentamethyl diethylene triamine, 1,4-diazabicyclo[2,2,2]-octane and N,N'-dimethyl piperazine; or metal salts such as iron(III)-chloride, zinc chloride, zinc-2-ethyl caproate, tin(II)-ethyl caproate, molybdenum glycolate and dialkyltin(IV) complexes, e.g., dibutyltin(IV)-dilaurate.

The coating compositions may also contain other additives such as pigments, dyes, fillers, levelling agents and solvents. The coating compositions may be applied to the substrate to be coated by conventional methods such as painting, rolling, pouring or spraying.

Coating compositions containing the blocked polyisocyanates according to the invention provide coatings which adhere surprisingly well to a variety of materials including metal substrates and basecoats (especially those used in the automotive industry), and are very resistant to abrasion. Furthermore, they are characterized by high hardness, elasticity, very good resistance to chemicals, high gloss, excellent weather resistance, excellent environmental etch resistance and good pigmenting qualities.

The invention is further illustrated, but is not intended to be limited by the following examples in which all parts and percentages are by weight unless otherwise specified. Isocyanate contents and equivalents weights are based on the weight of the solution unless otherwise specified.

EXAMPLES

Half-blocked isocyanate 1

The reaction product of one mole of 2,4-toluylene diisocyanate with one mole of 2-ethyl hexanol.

Hydroxy aspartate ester 172.0 parts of diethyl maleate (DEM), 50% in ethanol, were charged into a flask under nitrogen and then 61.0 parts of ethanolamine were added dropwise to the maleate while the temperature was maintained at 25° C. The reaction was completed over a time period of 7 hours. Ethanol was removed using a Brinkmann Rotavapor.

Bis-aspartate 1

210 parts of bis-(4-aminocyclohexyl)-methane (1.0 mole) were added dropwise with stirring to 344 parts of maleic acid diethylester (2.0 moles) that were previously charged at ambient temperature to a 1 L three necked flask equipped with a stirrer, thermometer and an addition funnel. The amine was added at a rate such that the exotherm did not increase the temperature of the reaction mixture above 50° C. Upon complete addition the contents of the reaction flask were maintained at 50° C. for a period of 12 hours. The resulting product was a clear, colorless liquid having a viscosity of about 1500 mPa.s (25° C.) and an amine equivalent weight of about 277.

EXAMPLE 1

Blocked polyisocyanate from half-blocked isocyanate 1 and hydroxy aspartate 1

68.93 parts of half-blocked isocyanate 1 were added dropwise to 61.25 parts of hydroxy aspartate 1 (NH:NCO equivalent ratio 1:1) at 80° C. The reaction was allowed to continue at this temperature for 1 hour after which the temperature was raised to 120° C. under vacuum during which ethanol was collected as a distillate. The presence of ethanol is evidence of the formation of hydantoin groups. This finding was confirmed by IR. The resulting product was solid at room temperature and had an amine number of 0 and an OH number of 80.

EXAMPLE 2

Blocked polyisocyanate from half-blocked isocyanate 1 and bis-aspartate 1

88.84 parts (0.29 moles) of half-blocked isocyanate 1 were added dropwise to 161.16 parts (0.29 moles) of bis-aspartate 1 (NH:NCO equivalent ratio 2:1) at 80° C. under a nitrogen blanket. The reaction was allowed to continue at this temperature for 1 hour after which the temperature was raised to 120° C. and 5000 ppm of acetic acid as catalyst was added to the mixture. The reaction was continued for 2 to 3 hours until the IR spectrum showed the completion of hydantoin formation. After completion of the reaction 9.0 parts of ethanol was collected under vacuum as distillate. The resulting product was solid and had an equivalent weight of about 813 and an NH number of about 69. When reduced to 70% solids in methyl isobutyl ketone, the resulting product had a viscosity of 405 mPa.s at 25° C., an equivalent weight of 1161.5 and an NH number of 48.3.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A blocked polyisocyanate containing at least one isocyanate group which is reversibly blocked with a monofunctional blocking agent for isocyanate groups and at least one isocyanate group in the form of a thermally stable hydantoin group, wherein the blocked polyisocyanate corresponds to the formula

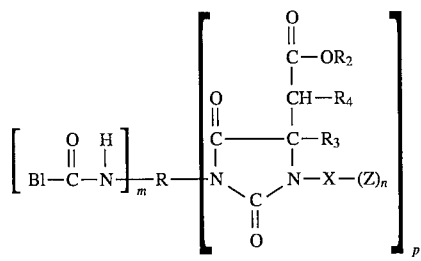 (I)

wherein

X represents an organic group which has a valency of n+1 and is inert towards isocyanate groups at a temperature of 100° C. or less, R represents the residue obtained by removing the isocyanate groups from a polyisocyanate having a functionality of m+p, $R_2$ represents an optionally substituted hydrocarbon radical, $R_3$ and $R_4$ are identical or different and represent hydrogen or organic groups which are inert towards isocyanate groups at a temperature of 100° C. or less, Bl represents the residue of a reversible, monofunctional blocking agent for isocyanate groups, m has a value of 1 to 5, n has a value of 1 to 3, p has a value of 1 to 5, m+p is 2 to 6 and Z represents —OH, —COOH, a polymer backbone or a group corresponding to the formula

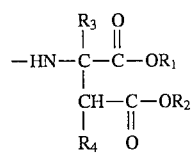

wherein $R_1$ represents an optionally substituted hydrocarbon radical.

2. The blocked polyisocyanate of claim 1 wherein $R_1$ and $R_2$ are the same or different and represent alkyl groups having 1 to 9 carbons, $R_3$ and $R_4$ represent hydrogen and n+m is 2.

3. The blocked polyisocyanate of claim 1 wherein m+p is 2.

4. The blocked polyisocyanate of claim 2 wherein m+p is 2.

5. The blocked polyisocyanate of claim 1 wherein R represents the residue obtained by removing the isocyanate groups from a diisocyanate having isocyanate groups of different reactivity.

6. The blocked polyisocyanate of claim 2 wherein R represents the residue obtained by removing the isocyanate groups from a diisocyanate having isocyanate groups of different reactivity.

7. The blocked polyisocyanate of claim 3 wherein R represents the residue obtained by removing the isocyanate groups from a diisocyanate having isocyanate groups of different reactivity.

8. The blocked polyisocyanate of claim 4 wherein R represents the residue obtained by removing the isocyanate groups from a diisocyanate having isocyanate groups of different reactivity.

9. A coating composition containing the blocked polyisocyanate of claim 1 and an isocyanate-reactive component.

* * * * *